United States Patent [19]

Moriyasu et al.

[11] Patent Number: 5,409,886
[45] Date of Patent: Apr. 25, 1995

[54] 3-PYRROLINE-2-ONE DERIVATIVES AND HERBICIDAL COMPOSITIONS CONTAINING SAME

[75] Inventors: Koichi Moriyasu; Hideyuki Akieda; Harumichi Aoki; Makoto Suzuki; Shingo Matsuo; Yasunaga Iwasaki; Sadafumi Koda; Kanji Tomiya, all of Mobara, Japan

[73] Assignee: Mitsui Toatsu Chemicals, Incorporated, Tokyo, Japan

[21] Appl. No.: 195,200

[22] Filed: Feb. 14, 1994

[30] Foreign Application Priority Data

Feb. 18, 1993 [JP] Japan ................. 5-028827
May 18, 1993 [JP] Japan ................. 5-115652
Nov. 15, 1993 [JP] Japan ................. 5-284655

[51] Int. Cl.$^6$ .................... C07D 207/38; A01N 43/36
[52] U.S. Cl. ..................... 504/283; 548/543
[58] Field of Search ............... 548/543; 504/283

[56] References Cited

U.S. PATENT DOCUMENTS

| | | | |
|---|---|---|---|
| 3,799,929 | 3/1974 | Holmes | 260/287 R |
| 4,680,299 | 7/1987 | Hesson | 514/311 |
| 4,847,381 | 7/1989 | Sutherland et al. | 546/156 |
| 4,861,783 | 8/1989 | Ackerman et al. | 514/311 |
| 4,968,701 | 11/1990 | Ackerman et al. | 546/176 X |
| 4,968,702 | 11/1990 | Poletto et al. | 514/313 |
| 5,006,157 | 4/1991 | Ohba et al. | 71/95 |
| 5,204,329 | 4/1993 | Ackerman et al. | 514/15 |

FOREIGN PATENT DOCUMENTS

WO9220642  11/1992  WIPO .

OTHER PUBLICATIONS

N. P. Buu–Hoi and Lavit, J. Chem. Soc., 2412 (1956).

N. P. Buu–Hoi and Cagniant, Chem. Ber., 76, 1269, (1943).

Ngyuyen et al. Chi Hoa Hoc, 27(1), 27, (1989); CA112(13):115589 (1990).

*Primary Examiner*—David B. Springer
*Attorney, Agent, or Firm*—Oblon, Spivak, McClelland, Maier & Neustadt

[57] ABSTRACT

A herbicidal composition is here disclosed which exerts an excellent herbicidal activity and which is harmless to paddy rice.

A 1-[1-methyl-1-(substituted phenyl)ethyl]-4,5-dimethyl-3-(substituted phenyl)-3-pyrroline-2-one derivative represented by the formula (I)

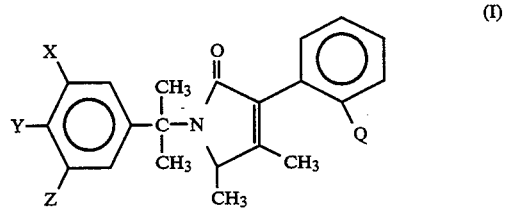

(wherein X is a chlorine atom, fluorine atom or bromine atom; Y is a hydrogen atom, fluorine atom, chlorine atom or methoxy group; Z is a hydrogen atom, fluorine atom, bromine atom or chlorine atom; and Q is a hydrogen atom or fluorine atom)

is a novel compound, and the herbicidal composition containing this compound as a herbicidally active ingredient has the strong activity and high selectivity as the herbicidal composition for paddy fields.

10 Claims, No Drawings

3-PYRROLINE-2-ONE DERIVATIVES AND HERBICIDAL COMPOSITIONS CONTAINING SAME

BACKGROUND OF THE INVENTION (i) Field of the Invention

The present invention relates to a novel 3-pyrroline-2-one derivative and a herbicidal composition containing this derivative as a herbicidally active ingredient particularly suitable for paddy fields. More specifically, it relates to a method for utilizing the 3-pyrroline-2-one derivative as the herbicidal composition for paddy fields.

(ii) Description of the Related Art

Heretofore, some 3-pyrroline derivatives having a herbicidal activity have been disclosed. For example, U.S. Pat. No. 5,006,157 has disclosed a compound represented by the formula

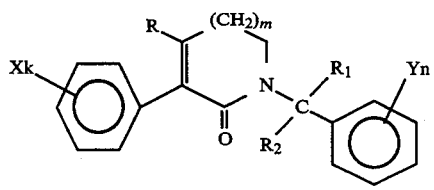

as a herbicidal composition, and this pyrroline compound is extremely active when used in a paddy field and shows a wide herbicidal spectrum. However, in the case that water moves downward owing to a certain external factor, e.g., water leak, this compound tends to be seriously chemically injurious to paddy rice, and for this reason, it is difficult to use the above-mentioned compound in the paddy field.

In recent years, a highly selective herbicidal composition which is not injurious to crops and which can kill only weeds has been strongly desired. Furthermore, as the herbicidal composition for paddy fields, an effective herbicidal composition has been desired which can surely kill tough tenacious weeds such as barnyard grass (Echinochloa), bulrush (*Scirpus juncoides*), monochoria (*Monochoria vaginalis*) and water nutgrass (*Cyperus serotinus*). In addition, it has been strongly desired to develop a herbicidal composition which can be used at any time of from the pre-emergence of the weeds to the growing period of the emerged weeds without any restriction on a use period and which has a long duration of the effect.

Under such circumstances, in the actual paddy field, there are various external factors which have an influence on the effect and the chemically injurious action by the herbicidal composition. Examples of the external factors include the soil quality of the paddy field, weather conditions such as temperature and light, the depth of submergence, water leak, the movement of water due to inflow and outflow, and a difference of the planting depth of the rice. These factors function singly or in an intricately linked combination to have a large influence on the effect of the herbicidal composition to the weeds, the chemical injury to the crops, the stability of the effect and the like. Of these influence factors, the most important one is the water leak. In most of the paddy fields in which the water leak occurs, in practice, the use of the herbicidal composition must be noticeably restricted owing to the occurrence of the chemical injury and the fluctuation of the effect which are caused by the downward movement of water and the herbicidal composition.

Therefore, the present invention intends to provide a selective herbicidal composition which is not injurious to the rice in the paddy field, has a wide herbicidal spectrum in a low application rate, is usable in a wide period of from the pre-emergence of the weeds to the growing period of the emerged weeds, and keeps the high effect and the low chemical injury even under an external factor such as the water leak.

SUMMARY OF THE INVENTION

The present inventors have conducted the research of 3-pyrroline derivatives with the intention of solving the above-mentioned problems, and as a result, we have found that a novel 3-pyrroline-2-one derivative is very excellent as a herbicidal composition, no chemically injurious to rice (*Oryza sativa*) which is an useful crop, and has an effect that an effect and the chemically injurious action do not fluctuate even under an external factor such as the water leak.

That is, the present invention is directed to a 3-pyrroline-2-one derivative represented by the formula (I)

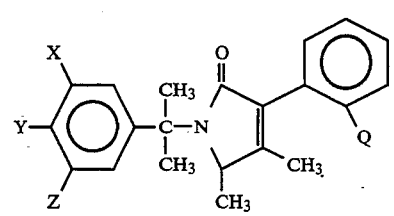

(I)

(wherein X is a chlorine atom, fluorine atom or bromine atom; Y is a hydrogen atom, fluorine atom, chlorine atom or methoxy group; Z is a hydrogen atom, fluorine atom, bromine atom or chlorine atom; and Q is a hydrogen atom or fluorine atom), a herbicidal composition containing this derivative, and a method for using the herbicidal composition.

Another aspect of the present invention is directed to a 3-pyrroline-2-one derivative represented by the above-mentioned formula (I) wherein X is a chlorine atom, Y is a hydrogen atom, Z is a hydrogen atom or chlorine atom, and Q is a hydrogen atom or fluorine atom, a herbicidal composition containing this derivative, and a method for using the herbicidal composition.

Still another aspect of the present invention is directed to a 3-pyrroline-2-one derivative represented by the above-mentioned formula (I) wherein each of X and Y is a chlorine atom, Z is a hydrogen atom, and Q is a hydrogen atom or fluorine atom, a herbicidal composition containing this derivative, and a method for using the herbicidal composition.

DETAILED DESCRIPTION OF THE INVENTION AND PREFERRED EMBODIMENT

A 3-pyrroline-2-one derivative of the present invention is a novel compound, and this derivative can be prepared by treating an amide derivative represented by the formula (II)

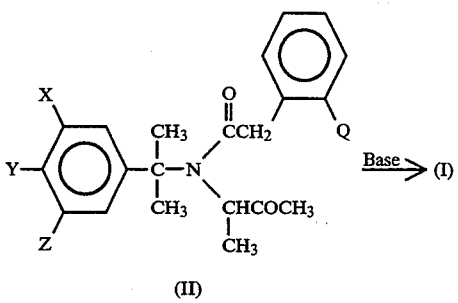

(wherein X is a chlorine atom, fluorine atom or bromine atom; Y is a hydrogen atom, fluorine atom, chlorine atom or methoxy group; Z is a hydrogen atom, fluorine atom, bromine atom or chlorine atom; and Q is a hydrogen atom or fluorine atom) with a suitable base to proceed to an intramolecular aldol condensation reaction.

Examples of the suitable base which can be used in the above-mentioned reaction include hydroxides of alkali metals such as sodium hydroxide, potassium hydroxide and lithium hydroxide; hydroxides of alkaline earth metals such as calcium hydroxide and barium hydroxide; alkali metals such as metallic sodium, metallic potassium and metallic lithium; hydrides of metals such as sodium hydride and lithium hydride; alcoholates such as t-butoxy potassium and sodium methoxide; and organic bases such as picoline, quinoline and 1,8-diazabicyclo[5.4.0]undecene-7 (DBU).

The above-mentioned reaction can be carried out in a suitable solvent or a non-solvent. Examples of the suitable solvent include aromatics such as benzene, toluene and xylene; ethers such as dioxane, tetrahydrofuran and diethyl ether; esters such as ethyl acetate and butyl acetate; lower alcohols such as methanol, ethanol, propanol and butanol; and non-protonic polar solvents such as dimethylformamide and dimethylacetamide. Reaction temperature is in the range of from −70° to 170° C., and the reaction may be carried out at the reflux temperature of the solvent.

The amide derivative represented by the formula (II) can be prepared in accordance with a method shown by the following reaction formula:

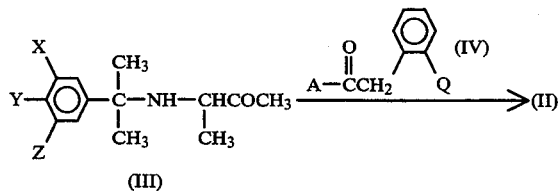

That is, the amide derivative can be prepared by reacting an aminoketone derivative represented by the formula (III) with a carboxylic acid derivative represented by the formula (IV) (wherein X, Y, Z and Q are as defined above, and A is a halogen atom) in the presence of a suitable base.

This reaction is carried out in the absence of any solvent or in a suitable solvent. Examples of the suitable solvent include aromatics such as benzene, toluene, xylene, chlorobenzene and dichlorobenzene; halogenated hydrocarbons such as dichloromethane, chloroform and carbon tetrachloride; ethers such as diethyl ether, tetrahydrofuran and dioxane; and esters such as ethyl acetate and butyl acetate. Examples of the suitable base include triethylamine, pyridine, dimethylaniline, diisobutylethylamine, sodium carbonate, potassium carbonate and sodium hydrogencarbonate. This reaction proceeds at an optional temperature.

The aminoketone derivative of the formula (III) can be prepared by reacting an α,α-dimethylbenzylamine derivative with 3-halogeno-2-butanone, and the carboxylic acid derivative represented by the formula (IV) is a commercially available product.

The herbicidal composition containing the thus obtained compound of the present invention as a herbicidally active ingredient has, as its functional characteristics, an excellent herbicidal effect to harmful weeds in most of the paddy fields, for example, gramineous weeds such as barnyard grass (Echinochloa), cyperaceous weeds such as *Cyperus microiria* and bulrush (*Scirpus juncoides*), anual broadleaf weeds such as monochoria (*Monochoria vaginalis*) and perennial broadleaf weeds such as *Sagittaria pygmaea*. On the other hand, the herbicidal composition is not injurious to rice (*Oryza sativa*) which is an useful crop. Furthermore, the herbicidal composition regarding the compound of the present invention can be effectively used in all applications such as submerged soil application, soil application and soil incorporation in the long term of from the pre-emergence of weeds to the growing period of the developed weeds.

The compound according to the invention of the present application is different from compounds such as 3-pyrroline derivatives and tetrahydropyridine derivatives disclosed in the above-mentioned prior art (Japanese Patent Application Laid-open No. 204855/1991) in that a methyl group is present at the 5-position of a pyrroline ring. For the improvement of the performance of the herbicidal composition, the presence of the methyl group at the 5-position of the pyrroline ring is very significant. When the compound of the present invention is used as the herbicidal composition, the chemical injury scarcely comes out even when water leak is present and the fluctuation of the effect is scarcely observed, and so the herbicidal composition can be used safely and effectively even in the paddy field of the water leak, as will be apparent from the undermentioned test examples. Moreover, when the chemical injury is observable at the time of the shallow planting of the paddy rice is also quite slight.

When used as the herbicidal composition, the compound represented by the formula (I) regarding the present invention is mixed with an inert liquid carrier or solid carrier, formulated in the form of powder, granules, wettable powder, emulsion, flowable formulation or the like those are employed in conventional art, and then used. If necessary in the formulation, auxiliary agents can be added.

The carrier may be in the state of a solid or a liquid, and no particular restriction is put on the carrier, so long as it can be conventionally used as agents for agriculture and horticulture. Examples of the solid carrier include a mineral powder such as clay, talc, bentonite, calcium carbonate, diatomaceous earth and white carbon, vegetable powders such as a soybean powder and starch, and high polymer compounds such as petroleum resin, polyvinyl alcohol and polyalkylene glycols, urea and waxes. Furthermore, examples of the liquid carrier include various organic solvents such as xylene, methylnaphthalene and alkylbenzenes, various oils such as vegetable oils, and water.

Examples of the auxiliary agents include surfactants usable in agents for agriculture and horticulture, binders (e.g., lignin sulfonic acid, alginic acid, polyvinyl alcohol, gum arabi and CMC sodium) and stabilizers (e.g., a phenolic compound, thiol compound or higher fatty acid ester for the prevention of oxidation, a phosphate as a pH regulator, and in a certain case, a light stabilizer), and they can be used singly or in combination. In some cases, an industrial germicide or an antibacterial fungicide can be added for the control of bacteria and fungi.

Examples of the surfactant include non-ionic, anionic, cationic and amphoteric surfactants, which can be suitably used singly or in combination. A preferable example of the non-ionic surfactant can be obtained by adding ethylene oxide or propylene oxide to an alkylphenol, higher alcohol, alkylnaphthol, higher fatty acid, fatty acid ester or the like. Preferable examples of the anionic surfactant are an alkylsulfonate salt, alkyl sulfate ester salt, phosphate ester salt or the like of an alkylphenol, alkylnaphthol, higher alcohol, higher fatty acid, fatty acid ester or the like. A lignine sulfonate salt is also one preferable example.

The content of the compound represented by the formula (I) in the herbicidal composition of the present invention depends upon the type of the formulation. In general, it is 0.01–20% by weight in the state of a powder, 1–50% by weight in a wettable powder, 0.01–10% by weight in granules, 0.1–50% by weight in an emulsion, 0.1–50% by weight in a flowable formulation and 1–50% by weight in a dry flowable formulation. Preferably, it is 0.1–3% by weight in a powder, 10–40% by weight in a wettable powder, 0.1–5% by weight in granules, 1–30% by weight in an emulsion, 1–30% by weight in a flowable formulation and 10–40% by weight in a dry flowable formulation.

The content of the auxiliary agents is 0–80% by weight, and the content of the carrier is a value obtained by balance of the content of the herbicidally active ingredient compound and the auxiliary agents from 100% by weight.

The herbicidal composition containing the compound of the present invention represented by the formula (I) as the herbicidally active ingredient, needless to say, can be mixed with one or more of other herbicidal compositions, agricultural chemicals such as a fungicide, an insecticide and a plant growth regulator, a fertilizer, a soil improver, and the like. In addition, the herbicidal composition can also be prepared in the state of a formulation mixed with these additives, and in some cases, a synergistic effect can be obtained.

The amount of the compound according to the present invention which is applied to soil for the purpose of killing weeds depends upon the growth stage of the weeds, environmental conditions and the type of formulation, but it can be suitably selected within the range of from 0.005 to 2 kg, preferably from 0.01 to 1 kg, more preferably from 0.025 to 0.4 kg per hectare in terms of the weight of the compound itself.

Next, methods for preparing compounds of the present invention will be described in detail in reference to examples.

EXAMPLE 1

Synthesis of 1-[1-methyl-1-(3-chloro-5-fluorophenyl)ethyl]-4,5-dimethyl-3-(2-fluorophenyl)-3-pyrroline-2-one [Compound No. 1]

To 20 ml of dichloromethane were added 3.0 g of N-[1-methyl-1-(3-chloro-5-fluorophenyl)ethyl]-N-(1-methyl-2-oxopropyl)amine and 3.5 g of pyridine, and 3.0 g of (2-fluorophenyl)acetyl chloride was then added dropwise thereto at 5° to 10° C. After stirring at room temperature for 1 hour, a saturated aqueous sodium hydrogencarbonate solution was added, followed by extraction with dichloromethane. After dried over anhydrous sodium sulfate, the solution was concentrated by evaporation, and the resulting oil was dissolved in 20 ml of ethyl acetate. Next, 10 ml of a 28% methanol solution of sodium methylate was added thereto, and after stirring under reflux for 15 minutes, the temperature of the solution was returned to room temperature and water was then added, followed by extraction with ethyl acetate. Afterward, the solution was washed with 12% hydrochloric acid and a saturated aqueous solution of sodium hydrogencarbonate, and then dried over anhydrous sodium sulfate. Next, the solution was condensed by an evaporator, and then subjected to silica gel chromatography to obtain 2.2 g of 1-[1-methyl-1-(3-chloro-5-fluorophenyl)ethyl]-4,5-dimethyl-3-(2-fluorophenyl)-3-pyrroline-2-one.

IR $\nu$ film cm$^{-1}$: 1664

NMR (270 MHz, CDCl$_3$) $\delta$ ppm: 1.43 (3H, d, J=6.6 Hz), 1.80 (3H, s), 1.84 (3H, s), 1.99 (3H, s), 4.27 (1H, q, J=6.6 Hz), 6.91–7.18 (4H, m), 7.25–7.40 (3H, m).

The same procedure as in Example 1 was used to synthesize 1-[1-methyl-1-(substituted phenyl)ethyl]-4,5-dimethyl-3-(substituted phenyl)-3-pyrroline-2-one derivatives. The names and physical properties of the obtained compounds are as follows:

1-[1-methyl-1-(3-chloro-5-fluorophenyl)ethyl]-4,5-dimethyl-3-phenyl-3-pyrroline-2-one [Compound No. 2]

NMR (270 MHz, CDCl$_3$) $\delta$ ppm: 1.39 (3H, d, J=6.6 Hz), 1.82 (3H, s), 1.84 (3H, s), 2.02 (3H, s), 4.24 (1H, q, J=6.6 Hz), 6.96–7.45 (8H, m).

IR $\nu$ film cm$^{-1}$: 1683.

1-[1-methyl-1-(3-bromophenyl)ethyl]-4,5-dimethyl-3-(2-fluorophenyl)-3-pyrroline-2-one [Compound No. 3]

NMR (270 MHz, CDCl$_3$) $\delta$ ppm: 1.35 (3H, d, J=6.6 Hz), 1.84 (3H, s), 1.87 (3H, s), 1.96 (3H, s), 4.22 (1H, q, J=6.6 Hz), 7.05–7.42 (7H, m), 7.51 (1H, t, J=2.0 Hz).

IR $\nu$ film cm$^{-1}$: 1683.

1-[1-methyl-1-(3-bromophenyl)ethyl]-4,5-dimethyl-3-phenyl-3-pyrroline-2-one [Compound No. 4]

NMR (270 MHz, CDCl$_3$) $\delta$ ppm: 1.33 (3H, d, J=6.9 Hz), 1.84 (3H, s), 1.86 (3H, s), 2.08 (3H, s), 4.18 (1H, q, J=6.9 Hz), 7.15–7.45 (8H, m), 7.51 (1H, t, J=2.0 Hz).

IR $\nu$ film cm$^{-1}$: 1685.

1-[1-methyl-1-(3-bromo-4-fluorophenyl)ethyl]-4,5-dimethyl-3-(2-fluorophenyl)-3-pyrroline-2-one [Compound No. 5]

NMR (270 MHz, CDCl$_3$) δ ppm: 1.35 (3H, d, J=6.6 Hz), 1.83 (3H, s), 1.85 (3H, s), 1.97 (3H, s), 4.24 (1H, q, J=6.6 Hz), 6.97–7.08 (2H, m), 7.25–7.40 (3H,m), 7.54–7.65 (2H, m).

IR ν film cm$^{-1}$: 1683.

1-[1-methyl-1-(3-bromo-4-fluorophenyl)ethyl]-4,5-dimethyl-3-phenyl-3-pyrroline-2-one [Compound No. 6]

NMR (270 MHz, CDCl$_3$) δ ppm: 1.36 (3H, d, J=6.6 Hz), 1.83 (3H, s), 1.85 (3H, s), 2.09 (3H, s), 4.20 (1H, q, J=6.6 Hz), 7.04 (1H, t, J=8.8 Hz), 7.25–7.43 (6H,m), 7.53–7.58 (1H, m).

IR ν film cm$^{-1}$: 1685.

1-[1-methyl-1-(3-chloro-4-fluorophenyl)ethyl]-4,5-dimethyl-3-(2-fluorophenyl)-3-pyrroline-2-one [Compound No. 7]

NMR (270 MHz, CDCl$_3$) δ ppm: 1.38 (3H, d, J=6.6 Hz), 1.83 (3H, s), 1.85 (3H, s), 1.97 (3H, d, J=2.9 Hz), 4.24 (1H, dq, J=6.6 Hz, 2.9 Hz), 7.00–7.45 (7H,m).

IR ν KBr cm$^{-1}$: 1668
m.p.: 124.0°–126.0° C.

1-[1-methyl-1-(3-chloro-4-fluorophenyl)ethyl]-4,5-dimethyl-3-phenyl-3-pyrroline-2-one [Compound No. 8]

NMR (270 MHz, CDCl$_3$) δ ppm: 1.37 (3H, d, J=6.6 Hz), 1.82 (3H, s), 1.84 (3H, s), 2.09 (3H, s), 4.20 (1H, q, J=6.6 Hz), 7.06 (1H, t, J=8.1 Hz), 7.24–7.43 (7H, m).

IR ν KBr cm$^{-1}$: 1669
m.p.: 123.5°–126.0° C.

1-[1-methyl-1-(3,4,5-trichlorophenyl)ethyl]-4,5-dimethyl-3-(2-fluorophenyl)-3-pyrroline-2-one [Compound No. 9]

NMR (270 MHz, CDCl$_3$) δ ppm: 1.49 (3H, d, J=6.6 Hz), 1.77 (3H, s), 1.81 (3H, s), 2.00 (3H, d, J=2.2 Hz), 4.25–4.35 (1H, m), 6.95–7.45 (6H, m).

IR ν film cm$^{-1}$: 1684.

1-[1-methyl-1-(3,4,5-trichlorophenyl)ethyl]-4,5-dimethyl-3-phenyl-3-pyrroline-2-one [Compound No. 10]

NMR (270 MHz, CDCl$_3$) δ ppm: 1.47 (3H, d, J=6.7 Hz), 1.78 (3H, s), 1.81 (3H, s), 2.12 (3H, s), 4.21–4.23 (1H, m), 7.28–7.42 (7H, m).

IR ν neat cm$^{-1}$: 1681.

1-[1-methyl-1-(3,5-dichloro-4-methoxyphenyl)ethyl]-4,5-dimethyl-3-(2-fluorophenyl)-3-pyrroline-2-one [Compound No. 11]

NMR (270 MHz, CDCl$_3$) δ ppm: 1.44 (3H, d, J=6.6 Hz), 1.70 (3H, s), 1.78 (3H, s), 1.99 (3H, d, J=2.2 Hz), 3.88 (3H, s), 4.24 (1H, dq, J=6.6 Hz, 2.2 Hz), 7.05–7.17 (3H, m), 7.26–7.40 (3H, m).

IR ν film cm$^{-1}$: 1683.

1-[1-methyl-1-(3,5-dichloro-4-methoxyphenyl)ethyl]-4,5-dimethyl-3-phenyl-3-pyrroline-2-one [Compound No. 12]

NMR (270 MHz, CDCl$_3$) δ ppm: 1.43 (3H, d, J=5.9 Hz), 1.79 (3H, s), 1.82 (3H, s), 2.11 (3H, s), 3.87 (3H, s), 4.21 (1H, q, J=5.9 Hz), 7.20–7.53 (7H, m).

IR ν neat cm$^{-1}$: 1682.

1-[1-methyl-1-(3-fluorophenyl)ethyl]-4,5-dimethyl-3-(2-fluorophenyl)-3-pyrroline-2-one [Compound No. 13]

NMR (270 MHz, CDCl$_3$) δ ppm: 1.34 (3H, d, J=6.6 Hz), 1.85 (3H, s), 1.88 (3H, s), 1.95 (3H, s), 4.24 (1H, q, J=6.6 Hz), 6.87–6.94 (1H, m), 7.05–7.42 (7H,m).

IR ν KBr cm$^{-1}$: 1665
m.p.: 102.4°–106.3° C.

1-[1-methyl-1-(3-fluorophenyl)ethyl]-4,5-dimethyl-3-phenyl-3-pyrroline-2-one [Compound No. 14]

NMR (270 MHz, CDCl$_3$) δ ppm: 1.32 (3H, d, J=6.6 Hz), 1.85 (3H, s), 1.87 (3H, s), 2.07 (3H, s), 4.19 (1H, q, J=6.6 Hz), 6.83–6.95 (1H, m), 7.05–7.49 (8H,m).

IR ν KBr cm$^{-1}$: 1668
m.p.: 115.7°–116.6° C.

1-[1-methyl-1-(3,4-difluorophenyl)ethyl]-4,5-dimethyl-3-(2-fluorophenyl)-3-pyrroline-2-one [Compound No. 15]

NMR (270 MHz, CDCl$_3$) δ ppm: 1.38 (3H, d, J=6.8 Hz), 1.83 (3H, s), 1.87 (3H, s), 1.98 (3H, s), 4.25 (1H, q, J=6.8 Hz), 7.00–7.39 (7H,m).

IR ν KBr cm$^{-1}$: 1667
m.p.: 134.0°–139.0° C.

EXAMPLE 2

Synthesis of 1-[1-methyl-1-(3-chlorophenyl)ethyl]-4,5-dimethyl-3-(2-fluorophenyl)-3-pyrroline-2-one To 20 ml of tetrahydrofuran were added 2.0 g of N-[1-methyl-1-(3-chlorophenyl)ethyl]-N-(1-methyl-2-oxopropyl)-2-(2-fluorophenyl)acetamide and 1.5 g of a 28% methanol solution of sodium methoxide, followed by stirring at room temperature for 5 minutes. After the solvent was distilled off, water was added, followed by extraction with ethyl acetate. After dried over anhydrous sodium sulfate, the solution was concentrated and then subjected to column chromatography to obtain 0.9 g of the desired 1-[1-methyl-1-(3-chlorophenyl)ethyl]-4,5-dimethyl-3-(2-fluorophenyl)-3-pyrroline-2-one.

The same procedure as in Example 2 was used to synthesize other compounds represented by the formula (I) regarding the present invention. The names and physical properties of these compounds are as follows:

Physical properties of 1-[1-methyl-1-(3-chlorophenyl)ethyl]-4,5-dimethyl-3-(2-fluorophenyl)-3-pyrroline-2-one [Compound No. 16]

NMR (400 MHz, CDCl$_3$) δ ppm: 1.35 (3H, d, J=6.6 Hz), 1.84 (3H, s), 1.87 (3H, s), 1.96 (3H, s), 4.23 (1H, q, J=6.6 Hz), 7.06–7.30 (6H, m), 7.36–7.41 (2H, m).

IR ν film (cm$^{-1}$): 1683.

Physical properties of 1-[1-methyl-1-(3-chlorophenyl)ethyl]-4,5-dimethyl-3-phenyl-3-pyrroline-2-one Compound No. 17]

NMR (400 MHz, CDCl$_3$) δ ppm: 1.34 (3H, d, J=6.6 Hz), 1.84 (3H, s), 1.87 (3H, s), 2.09 (3H, s), 4.19 (1H, q, J=6.6 Hz), 7.13–7.25 (2H, m), 7.27–7.31 (2H, m), 7.33–7.38 (3H, m), 7.41–7.45 (2H, m).

IR ν film (cm$^{-1}$): 1682.

Physical properties of 1-[1-methyl-1-(3,5-dichlorophenyl)ethyl]-4,5-dimethyl-3-(2-fluorophenyl)-3-pyrroline-2-one [Compound No. 18]

NMR (400 MHz, CDCl$_3$) δ ppm: 1.44 (3H, d, J=5.9 Hz), 1.80 (3H, s), 1.83 (3H, s), 1.99 (3H, s), 4.27 (1H, q, J=5.9 Hz), 7.06–7.17 (3H, m), 7.19–7.32 (3H, m), 7.34–7.38 (1H, m).

IR ν film (cm$^{-1}$): 1682.

EXAMPLE 3

Synthesis of 1-[1-methyl-1-(3,5-dichlorophenyl)ethyl]-4,5-dimethyl-3-phenyl-3-pyrroline-2-one [Compound No. 19]

To 15 ml of toluene were added 2.2 g of N-[1-methyl-1-(3,5-dichlorophenyl)ethyl]-N-(1-methyl-2-oxopropyl)-2-phenylacetamide and 3.5 g of 1,8-diazabicyclo[5.4.0]undecene-7 (DBU), followed by stirring at room temperature for 1 hour. After water was added, the solution was extracted with ethyl acetate, and then dried over anhydrous sodium sulfate. After the solvent was distilled off, the solution was subjected to silica gel column chromatography to obtain 1.1 g of the desired 1-[1-methyl-1-(3,5-dichlorophenyl)ethyl]-4,5-dimethyl-3-phenyl-3-pyrroline-2-one.

NMR (400 MHz, CDCl$_3$) δ ppm: 1.43 (3H, d, J=6.6 Hz), 1.79 (3H, s), 1.82 (3H, s), 2.11 (3H, s), 4.23 (1H, q, J=6.6 Hz), 7.19–7.31 (4H, m), 7.35–7.43 (4H, m).

IR ν film (cm$^{-1}$): 1684.

EXAMPLE 4

Synthesis of 1-[1-methyl-1-(3,4-dichlorophenyl)ethyl]-4,5-dimethyl-3-(2-fluorophenyl)-3-pyrroline-2-one [Compound No. 21]

To 20 ml of dichloromethane were added 3.0 g of N-[1-methyl-1-(3,4-dichlorophenyl)ethyl]-N-(1-methyl-2-oxopropyl)amine and 3.5 g of pyridine, and 4.0 g of 2-fluorophenylacetyl chloride was then added dropwise thereto at 5° to 10° C. After stirring at room temperature for 1 hour, a saturated aqueous sodium hydrogencarbonate solution was added, followed by extraction with dichloromethane. After dried over anhydrous sodium sulfate, the solution was concentrated by an evaporator, and the resulting oil was dissolved in 20 ml of ethyl acetate. Next, 10 ml of a 28% methanol solution of sodium methylate was added thereto, and after stirring under reflux for 15 minutes, the temperature of the solution was returned to room temperature and water was then added, followed by extraction with ethyl acetate. Afterward, the solution was washed with a 12% hydrochloric acid and a saturated aqueous solution of sodium hydrogencarbonate, and then dried over anhydrous sodium sulfate. Next, the solution was concentrated by an evaporator, and then subjected to silica gel chromatography to obtain 2.5 g of 1-[1-methyl-1-(3,4-dichlorophenyl)ethyl]-4,5-dimethyl-3-(2-fluorophenyl)-3-pyrroline-2-one.

m.p.: 137.0°–139.0° C.

IR ν film cm$^{-1}$: 1667.

The same procedure to Example 4 was used to synthesize 1-[1-methyl-1-(3,4-dichlorophenyl)ethyl]-4,5-dimethyl-3-phenyl-3-pyrroline-2-one [Compound No. 22] of the present invention. The physical properties of this compound are as follows:

NMR (400 MHz, CDCl$_3$) δ ppm: 1.39 (3H, d, J=6.5 Hz), 1.81 (3H, s), 1.84 (3H, s), 2.10 (3H, s), 4.21 (1H, q, J=6.5 Hz), 7.22–7.45 (8H, m).

m.p.: 134.0°–137.0° C.

IR ν film (cm$^{-1}$): 1683.

Furthermore, synthetic examples of intermediates, which are important to synthesize the compounds of the formula (I) of the present invention, will be described as reference examples.

REFERENCE EXAMPLE 1

Synthesis of N-[1-methyl-1-(3-chloro-5-fluorophenyl)ethyl]-N-(1-methyl-2-oxopropyl)amine To 20 ml of N,N-dimethylformamide were added 3.5 g of N-[1-methyl-1-(3-chloro-5-fluorophenyl)ethyl]amine, 3.0 g of potassium carbonate, 2.5 g of potassium iodide and 15.0 g of 3-chloro-2-butanone, followed by stirring at 80° C. for 1 hour. After insolubles were removed by filtration, 100 ml of water was added thereto, and the solution was then extracted with toluene. After dried over anhydrous sodium sulfate, the solution was concentrated by an evaporator, and then subjected to silica gel chromatography to obtain 3.6 g of the desired aminoketone.

IR ν film cm$^{-1}$: 3329, 1716 n$_D$ 24.9° C.: 1.4273.

REFERENCE EXAMPLE 2

Synthesis of N-[1-methyl-1-(3-chlorophenyl)ethyl]-N-(1-methyl-2-oxopropyl)-2-(2-fluorophenyl)acetamide In 30 ml of dichloromethane containing 4.0 g of pyridine, 5.0 g of 2-(2-fluorophenyl)acetyl chloride was added dropwise to 3.2 g of N-[1-methyl-1-(3-chlorophenyl)ethyl]-N-(1-methyl-2-oxopropyl)amine at 20° to 30° C. After stirring for 1 hour, the solution was poured into water, and then extracted with dichloromethane. Next, the solution was washed with a saturated aqueous sodium bicarbonate solution, dried over anhydrous sodium sulfate, concentrated by an evaporator, and then subjected to column chromatography to obtain 2.4 g of N-[1-methyl-1-(3chlorophenyl)ethyl]-N-(1-methyl-2-oxopropyl)-2-(2-fluorophenyl)acetamide.

REFERENCE EXAMPLE 3

Synthesis of N-[1-methyl-1-(3,5-dichlorophenyl)ethyl]-N-(1-methyl-2-oxopropyl)-2-phenylacetamide In 15 ml of dichloromethane containing 2.0 g of pyridine and 1.0 g of N-ethyl-N,N-diisopropylamine, 3.5 g of 2-phenylacetyl chloride was added dropwise to 2.5 g of N-[1-methyl-1-(3,5-dichlorophenyl)ethyl]-N-(1-methyl-2-oxopropyl)amine at room temperature. After stirring at room temperature for 1 hour, the solution was poured into water, and then extracted with ethyl acetate. Next, the solution was washed with a saturated aqueous sodium bicarbonate solution, dried over anhydrous magnesium sulfate, concentrated, and then subjected to column chromatography to obtain 1.7 g of N-[1-methyl-1-(3,5-dichlorophenyl)ethyl]-N-(1-methyl-2-oxopropyl)-2-phenylacetamide.

The same procedure as in Reference Example 2 or 3 was used to synthesize other acetamide derivatives represented by the formula (II). The names and physical properties of the obtained derivatives are as follows:

The physical properties of N-[1-methyl-1-(3-chlorophenyl)ethyl]-N-(1-methyl-2-oxopropyl)-2-(2-fluorophenyl)acetamide IR ν film (cm$^{-1}$): 1718, 1686 n$_D$ 20.8° C.: 1.5614.

The physical properties of N-[1-methyl-1-(3-chlorophenyl)ethyl]-N-(1-methyl-2-oxopropyl)-2-phenylacetamide IR $\nu$ film (cm$^{-1}$): 1717, 1687
$n_D$ 19.5° C.: 1.5732.

The physical properties of N-[1-methyl-1-(3,5-dichlorophenyl)ethyl]-N-(1-methyl-2-oxopropyl)-2-(2-fluorophenyl)acetamide IR $\nu$ film (cm$^{-1}$): 1716, 1690
$n_D$ 24.6° C.: 1.5723.

The physical properties of N-[1-methyl-1-(3,5-dichlorophenyl)ethyl]-N-(1-methyl-2-oxopropyl)-2phenylacetamide IR $\nu$ film (cm$^{-1}$): 1716, 1692
$n_D$ 20.6° C.: 1.5804.

REFERENCE EXAMPLE 4

Synthesis of N-[1-methyl-1-(3,5-dichlorophenyl)ethyl]-N-(1-methyl-2-oxopropyl)amine To 20 ml of N,N-dimethylformamide were added 3.5 g of N-[1-methyl-1-(3,5-dichlorophenyl)ethyl]amine, 3.0 g of potassium carbonate, 2.5 g of potassium iodide and 7.0 g of 3-chloro-2-butanone, followed by stirring at 80° C. for 1 hour. After insolubles were removed by filtration, 100 ml of water was added thereto, and the solution was then extracted with toluene. After dried over anhydrous sodium sulfate, the solution was concentrated by means of an evaporator, and then subjected to silica gel column chromatography to obtain 4.0 g of the desired aminoketone.

Furthermore, the same procedure as in Reference Example 4 was used to obtain other aminoketone derivatives represented by the formula (III). The names and physical properties of the obtained derivatives are as follows:

The physical properties of N-[1-methyl-1-(3chlorophenyl)ethyl]-N-(1-methyl-2-oxopropyl)amine IR $\nu$ film (cm$^{-1}$): 3324, 1716
$n_D$ 20.4° C.: 1.5165.

The physical properties of N-[1-methyl-1-(3,5-dichlorophenyl)ethyl]-N-(1-methyl-2-oxopropyl)amine IR $\nu$ film (cm$^{-1}$): 3324, 1716
$n_D$ 19.6° C.: 1.5351.

REFERENCE EXAMPLE 5

Synthesis of N-[1-methyl-1-(3,4-dichlorophenyl)ethyl]-N-(1-methyl-2-oxopropyl)amine To 20 ml of N,N-dimethylformamide were added 3.5 g of N-[1-methyl-1-(3,4-dichlorophenyl)ethyl]amine, 3.0 g of potassium carbonate, 2.5 g of potassium iodide and 17.0 g of 3-chloro-2-butanone, followed by stirring at 80° C. for 1 hour. After insolubles were removed by filtration, 100 ml of water was added thereto, and the solution was then extracted with toluene. After dried over anhydrous sodium sulfate, the solution was concentrated by an evaporator, and then subjected to silica gel column chromatography to obtain 3.8 g of the desired aminoketone.

IR $\nu$ film (cm$^{-1}$): 3324, 1717
$n_D$ 19.1° C.: 1.5245.

Next, formulation examples of the herbicides according to the present invention will be described.

FORMULATION EXAMPLE 1 (Wettable Powder)

A wettable powder was obtained by sufficiently grinding and mixing 20 parts by weight of Compound No. 1 of the present invention, 2 parts by weight of Neopelex (trade name, made by Kao Corporation; sodium dodecyl benzene sulfonate), 1 part by weight of Neugen EA80 (trade name, made by Sanyo Chemical Industries, Ltd.; polyoxyethylene nonylphenyl ether), 5 parts by weight of white carbon and 72 parts by weight of diatomaceous earth.

FORMULATION EXAMPLE 2 (Wettable Powder)

A wettable powder was obtained by sufficiently grinding and mixing 20 parts by weight of Compound No. 2 of the present invention, 2 parts by weight of sodium alkylbenzenesulfonate, 1 part by weight of a polyoxyethylene alkylphenyl ether and 77 parts by weight of Giecrite.

FORMULATION EXAMPLE 3 (Wettable Powder)

A wettable powder was obtained by thoroughly grinding and mixing 50 parts by weight of Compound No. 3 of the present invention, 5 parts by weight of white carbon, 6 parts by weight of polyoxyethylene alkylphenyl ether ammonium sulfate, 2 parts by weight sodium lignine sulfonate and 37 parts by weight of diatomaceous earth by the use of a jet-O-mizer.

FORMULATION EXAMPLE 4 (Powder)

A powder was obtained by thoroughly grinding and mixing 1 part by weight of Compound No. 7 of the present invention, 0.5 part by weight of Emulgen 910 (trade name, made by Kao Corporation; polyoxyethylene nonylphenyl ether) and 98.5 parts by weight of kaolin clay.

FORMULATION EXAMPLE 5 (Powder)

A powder was obtained by mixing and grinding 3 parts by weight of Compound No. 14 of the present invention, 3 parts by weight of sodium lignine sulfonate, 2 parts by weight of a polyoxyethylene alkylaryl ether and 92 parts by weight of clay.

FORMULATION EXAMPLE 6 (Granules)

0.3 part by weight of Compound No. 6 of the present invention, 2 parts by weight of Neopelex (trade name, as described above), 2 parts by weight of Sun Ekisu P252 (trade name, made by Sanyo-Kokusaku Pulp Co., Ltd.; sodium lignine sulfonate), 72.7 parts by weight of bentonite and 23 parts by weight of talc were thoroughly mixed. Afterward, water was added to the resultant mixture to wet the same, followed by extrusion of the mass through a small injection molding machine into pellets. After the pellets were dried at 30°–60° C. in air and then crushed into granules, the granules were then classified by a sifting machine to collect granules of 0.3–2 mm.

FORMULATION EXAMPLE 7 (Granules)

0.5 part by weight of Compound No. 7 of the present invention, 2 .parts by weight of Gosenol GL-05s (PVA made by Nippon Synthetic Chemical Industry Co., Ltd.), 2 parts of Sun Ekisu P252 (trade name, made by Sanyo-Kokusaku Pulp Co., Ltd.; sodium benzenesulfonate) and 95.5 parts of clay were thoroughly mixed, and afterward, water was then added to the mixture to wet the same, followed by extrusion of the mass through an injection molding machine into pellets. After the pellets were dried at 60°–90° C. in air and then crushed into granules, the granules were then classified by a sifting machine to collect granules of 0.3–1 mm.

FORMULATION EXAMPLE 8 (Emulsion)

An emulsion was obtained by mutually mixing and then dissolving 10 parts by weight of Compound No. 2 of the present invention, 10 parts by weight of Sorpole 800A (trade name, made by Toho Chemical Industries Co., Ltd.; a nonionic/anionic surfactant mixture) and 80 parts by weight of o-xylene.

FORMULATION EXAMPLE 9 (Wettable Powder)

The same procedure as in Formulation Example 1 was carried out except that Compound No. 1 was replaced with 20 parts by weight of Compound No. 16 of the present invention, to obtain a wettable powder.

FORMULATION EXAMPLE 10 (Wettable Powder)

The same procedure as in Formulation Example 2 was carried out except that Compound No. 2 was replaced with 20 parts by weight of Compound No. 17 of the present invention, to obtain a wettable powder.

FORMULATION EXAMPLE 11 (Wettable Powder)

The same procedure as in Formulation Example 3 was carried out except that Compound No. 3 was replaced with 50 parts by weight of Compound No. 18 of the present invention, to obtain a wettable powder.

FORMULATION EXAMPLE 12 (Powder)

The same procedure as in Formulation Example 4 was carried out except that Compound No. 4 was replaced with 1 part by weight of Compound No. 19 of the present invention, to obtain a powder.

FORMULATION EXAMPLE 13 (Powder)

The same procedure as in Formulation Example 5 was carried out except that Compound No. 1 was replaced with 3 parts by weight of Compound No. 16 of the present invention, to obtain a powder.

FORMULATION EXAMPLE 14 (Granules)

The same procedure as in Formulation Example 6 was carried out except that Compound No. 2 was replaced with 0.3 part by weight of Compound No. 17 of the present invention, to obtain granules.

FORMULATION EXAMPLE 15 (Granules)

The same procedure as in Formulation Example 7 was carried out except that Compound No. 3 was replaced with 0.5 part by weight of Compound No. 18 of the present invention, to obtain granules.

FORMULATION EXAMPLE 16 (Emulsion)

The same procedure as in Formulation Example 8 was carried out except that Compound No. 4 was replaced with 10 parts by weight of Compound No. 19 of the present invention, to obtain an emulsion.

FORMULATION EXAMPLE 17 (Wettable Powder)

The same procedure as in Formulation Example 1 was carried out except that Compound No. 1 was replaced with 20 parts by weight of Compound No. 21 of the present invention, to obtain a wettable powder.

FORMULATION EXAMPLE 18 (Wettable Powder)

The same procedure as in Formulation Example 2 was carried out except that Compound No. 2 was replaced with 20 parts by weight of Compound No. 22 of the present invention, to obtain a wettable powder.

FORMULATION EXAMPLE 19 (Wettable Powder)

The same procedure as in Formulation Example 3 was carried out except that Compound No. 1 was replaced with 50 parts by weight of Compound No. 21 of the present invention, to obtain a wettable powder.

FORMULATION EXAMPLE 20 (Powder)

The same procedure as in Formulation Example 4 was carried out except that Compound No. 2 was replaced with 1 part by weight of Compound No. 22 of the present invention, to obtain a powder.

FORMULATION EXAMPLE 21 (Powder)

The same procedure as in Formulation Example 5 was carried out except that Compound No. 1 was replaced with 3 parts by weight of Compound No. 21 of the present invention, to obtain a powder.

FORMULATION EXAMPLE 22 (Granules)

The same procedure as in Formulation Example 6 was carried out except that Compound No. 2 was replaced with 0.3 part by weight of Compound No. 22 of the present invention, to obtain granules.

FORMULATION EXAMPLE 23 (Granules)

The same procedure as in Formulation Example 7 was carried out except that Compound No. 1 was replaced with 0.5 part by weight of Compound No. 21 of the present invention, to obtain granules.

FORMULATION EXAMPLE 24 (Emulsion)

The same procedure as in Formulation Example 8 was carried out except that Compound No. 2 was replaced with 10 parts by weight of Compound No. 22 of the present invention, to obtain an emulsion.

Next, physiological tests of the herbicidal compositions according to the present invention will be described.

PHYSIOLOGICAL TEST 1

Treatment of Soil Under Submerged Condition (Pre-emergence Treatment)

1/500000-hectare Wagner pots were filled with soil, and they were put in water and the soil was then tilled. Afterward, seeds of *Echinochloa crusgalli*, bulrush (*Scirpus juncoides*), monochoria (*Monochoria vaginalis*) and false pimpernel (*Lindernia pyxidaria*) were sown under submerged condition. Two pairs of paddy rice (*Oryza sativa*) seedlings (2–3 leaf stage), which had been reared in advance, were transplanted to each pot and were allowed to grow in a green house, each pair being constituted of two rice seedlings. One day later (before the emergence of weeds), each pot was treated with a wettable powder which had been prepared by processing a predetermined amount of the test compound in accordance with the procedure described in Formulation Example 1. A submerged portion of each rice seedling was set to 3 cm, and from the next day after the treatment, water leak was carried out for 10 days. That is, water in each pot was allowed to drop through the bottom of the pot by the use of a glass tube so that a water surface might go down as much as 1 cm per day. The growing state of weeds and the injurious state to the rice were observed 30 days later. The results are summarized in Table 1. In this table, the damage degree of each test plant and the injurious degree to the paddy rice were determined by comparing the dry weight of the test plant with that of the corresponding plant in untreated pots, and they are denoted in accordance with the following standard.

| Growth rate (%) expressed in terms of the percentage of dry weight relative to the dry weight of untreated group | Rank |
|---|---|
| 0–5 | 10 |
| 6–10 | 9 |
| 11–20 | 8 |
| 21–30 | 7 |
| 31–40 | 6 |
| 41–60 | 5 |
| 61–70 | 4 |
| 71–80 | 3 |
| 81–90 | 2 |
| 91–95 | 1 |
| 96–100 | 0 |

In Physiological Test 1–9, Comparative Compounds A, B and C are, respectively.

A: 1-[1-methyl-1-(3-chlorophenyl)ethyl]-4-methyl-3-(2-fluorophenyl)-3-pyrroline-2-one
B: 1-[1-methyl-1-(3,4-dichlorophenyl)ethyl]-4-methyl-3-(2-fluorophenyl)-3-pyrroline-2-one
C: 1-[1-methyl-1-(3,5-dichlorophenyl)ethyl]-4-methyl-3-(2-fluorophenyl)-3-pyrroline-2-one (Comparative Compounds A, B and C are known compounds on U.S. Pat. No. 5,006,157)

Table 1 indicates that in this test, the herbicidal compositions regarding the present invention exerted higher herbicidal effects to the sample weeds in the paddy fields in spite of the low application rates, and they also exerted excellent safety to the paddy rice. On the contrary, Comparative Compounds A and B had a pharmaceutically injurious action on the paddy rice, when they were used in amounts capable of completely killing the weeds.

TABLE 1

| Compound No. | Application rate, kg/ha | Echinochloa crusgalli | Monochoria (Monochoria vaginalis) | False Bulrush (Scirpus juncoides) | pimpernel (Lindernia pyxidaria) | Rice (Oryza sativa) |
|---|---|---|---|---|---|---|
| 1 | 0.025 | 10 | 10 | 10 | 10 | 0 |
|   | 0.05  | 10 | 10 | 10 | 10 | 0 |
|   | 0.1   | 10 | 10 | 10 | 10 | 0 |
|   | 0.2   | 10 | 10 | 10 | 10 | 1 |
| 2 | 0.025 | 10 | 10 | 10 | 10 | 0 |
|   | 0.05  | 10 | 10 | 10 | 10 | 0 |
|   | 0.1   | 10 | 10 | 10 | 10 | 0 |
|   | 0.2   | 10 | 10 | 10 | 10 | 1 |
| 3 | 0.025 | 10 | 8  | 9  | 9  | 0 |
|   | 0.05  | 10 | 8  | 10 | 9  | 0 |
|   | 0.1   | 10 | 10 | 10 | 10 | 0 |
|   | 0.2   | 10 | 10 | 10 | 10 | 0 |
| 4 | 0.025 | 10 | 8  | 9  | 9  | 0 |
|   | 0.05  | 10 | 9  | 10 | 9  | 0 |
|   | 0.1   | 10 | 10 | 10 | 10 | 0 |
|   | 0.2   | 10 | 10 | 10 | 10 | 0 |
| 5 | 0.025 | 9  | 9  | 9  | 9  | 0 |
|   | 0.05  | 10 | 10 | 10 | 10 | 0 |
|   | 0.1   | 10 | 10 | 10 | 10 | 0 |
|   | 0.2   | 10 | 10 | 10 | 10 | 0 |
| 6 | 0.025 | 8  | 9  | 9  | 8  | 0 |
|   | 0.05  | 9  | 10 | 10 | 9  | 0 |
|   | 0.1   | 10 | 10 | 10 | 10 | 0 |
|   | 0.2   | 10 | 10 | 10 | 10 | 0 |
| 7 | 0.025 | 9  | 8  | 8  | 9  | 0 |
|   | 0.05  | 9  | 9  | 9  | 9  | 0 |
|   | 0.1   | 10 | 10 | 10 | 10 | 0 |
|   | 0.2   | 10 | 10 | 10 | 10 | 0 |
| 8 | 0.025 | 9  | 8  | 9  | 9  | 0 |
|   | 0.05  | 10 | 9  | 10 | 9  | 0 |
|   | 0.1   | 10 | 10 | 10 | 10 | 0 |
|   | 0.2   | 10 | 10 | 10 | 10 | 0 |
| 9 | 0.025 | 10 | 9  | 9  | 9  | 0 |
|   | 0.05  | 10 | 10 | 10 | 10 | 0 |
|   | 0.1   | 10 | 10 | 10 | 10 | 0 |
|   | 0.2   | 10 | 10 | 10 | 10 | 0 |
| 10 | 0.025 | 10 | 9  | 9  | 8  | 0 |
|    | 0.05  | 10 | 10 | 10 | 9  | 0 |
|    | 0.1   | 10 | 10 | 10 | 10 | 0 |
|    | 0.2   | 10 | 10 | 10 | 10 | 0 |
| 11 | 0.025 | 10 | 8  | 10 | 10 | 0 |
|    | 0.05  | 10 | 9  | 10 | 10 | 0 |
|    | 0.1   | 10 | 10 | 10 | 10 | 0 |
|    | 0.2   | 10 | 10 | 10 | 10 | 0 |
| 12 | 0.025 | 10 | 7  | 10 | 9  | 0 |
|    | 0.05  | 10 | 8  | 10 | 10 | 0 |
|    | 0.1   | 10 | 10 | 10 | 10 | 0 |
|    | 0.2   | 10 | 10 | 10 | 10 | 0 |
| 13 | 0.025 | 8  | 10 | 9  | 7  | 0 |
|    | 0.05  | 9  | 10 | 10 | 9  | 0 |
|    | 0.1   | 10 | 10 | 10 | 10 | 0 |
|    | 0.2   | 10 | 10 | 10 | 10 | 1 |

TABLE 1-continued

| Compound No. | Application rate, kg/ha | Echinochloa crusgalli | Monochoria (Monochoria vaginalis) | False Bulrush (Scirpus juncoides) | pimpernel (Lindernia pyxidaria) | Rice (Oryza sativa) |
|---|---|---|---|---|---|---|
| 14 | 0.025 | 8 | 9 | 9 | 7 | 0 |
|  | 0.05 | 9 | 10 | 10 | 9 | 0 |
|  | 0.1 | 10 | 10 | 10 | 10 | 0 |
|  | 0.2 | 10 | 10 | 10 | 10 | 1 |
| 15 | 0.025 | 8 | 9 | 9 | 8 | 0 |
|  | 0.05 | 9 | 9 | 10 | 9 | 0 |
|  | 0.1 | 10 | 10 | 10 | 9 | 0 |
|  | 0.2 | 10 | 10 | 10 | 10 | 1 |
| A | 0.025 | 8 | 7 | 8 | 7 | 1 |
|  | 0.05 | 9 | 8 | 9 | 8 | 2 |
|  | 0.1 | 10 | 10 | 10 | 9 | 4 |
|  | 0.2 | 10 | 10 | 10 | 10 | 6 |
| B | 0.025 | 7 | 7 | 7 | 8 | 1 |
|  | 0.05 | 8 | 8 | 9 | 9 | 3 |
|  | 0.1 | 9 | 9 | 10 | 9 | 4 |
|  | 0.2 | 10 | 10 | 10 | 10 | 6 |

PHYSIOLOGICAL TEST 2

Treatment of Soil Under Submerged Condition
(Growing Period Treatment)

1/500000-hectare Wagner pots were filled with soil, and they were put in water and the soil was then tilled. Afterward, seeds of *Echinochloa crusgalli*, bulrush (*Scirpus juncoides*), monochoria (*Monochoria vaginalis*) and false pimpernel (*Lindernia pyxidaria*) were sown under submerged condition. Two pairs of paddy rice (*Oryza sativa*) seedlings (2-3 leaf stage), which had been reared in advance, were transplanted to each pot and were allowed to grow in a green house, each pair being constituted of two rice seedlings. When *Echinochloa crusgalli* became bifoliate, each pot was treated with a wettable powder which had been prepared by processing a predetermined amount of the test compound in accordance with the procedure described in Formulation Example 2. A submerged portion of each rice seedling was set to 3 cm, and from the next day after the treatment, water leak was carried out for 10 days. That is, water in each pot was allowed to drop through the bottom of the pot by the use of a glass tube so that a water surface might go down as much as 1 cm per day. The growing state of weeds and the injurious state to the rice were observed 30 days later. The results are summarized in Table 2. In this table, the damage degree of each test plant and the injurious degree to the paddy rice are denoted in the same manner as in Physiological Test 1.

Table 2 indicates that in this test, the herbicidal compositions regarding the present invention exerted higher herbicidal effects to the sample weeds in the paddy fields in spite of the low application rates, and they also exerted excellent safety to the paddy rice. On the contrary, Comparative Compounds A and B had a pharmaceutically injurious action on the paddy rice, when they were used in amounts capable of completely killing the weeds.

TABLE 2

| Compound No. | Application rate, kg/ha | Echinochloa crusgalli | Monochoria (Monochoria vaginalis) | False Bulrush (Scirpus juncoides) | pimpernel (Lindernia pyxidaria) | Rice (Oryza sativa) |
|---|---|---|---|---|---|---|
| 1 | 0.025 | 10 | 9 | 10 | 10 | 0 |
|  | 0.05 | 10 | 10 | 10 | 10 | 0 |
|  | 0.1 | 10 | 10 | 10 | 10 | 0 |
|  | 0.2 | 10 | 10 | 10 | 10 | 0 |
|  | 0.4 | 10 | 10 | 10 | 10 | 1 |
| 2 | 0.025 | 10 | 9 | 10 | 10 | 0 |
|  | 0.05 | 10 | 10 | 10 | 10 | 0 |
|  | 0.1 | 10 | 10 | 10 | 10 | 0 |
|  | 0.2 | 10 | 10 | 10 | 10 | 1 |
|  | 0.4 | 10 | 10 | 10 | 10 | 2 |
| 3 | 0.025 | 9 | 8 | 8 | 9 | 0 |
|  | 0.05 | 10 | 9 | 9 | 10 | 0 |
|  | 0.1 | 10 | 10 | 10 | 10 | 0 |
|  | 0.2 | 10 | 10 | 10 | 10 | 0 |
|  | 0.4 | 10 | 10 | 10 | 10 | 0 |
| 4 | 0.025 | 8 | 8 | 9 | 9 | 0 |
|  | 0.05 | 9 | 9 | 10 | 10 | 0 |
|  | 0.1 | 10 | 10 | 10 | 10 | 0 |
|  | 0.2 | 10 | 10 | 10 | 10 | 0 |
|  | 0.4 | 10 | 10 | 10 | 10 | 0 |
| 5 | 0.025 | 8 | 8 | 8 | 9 | 0 |
|  | 0.05 | 9 | 9 | 9 | 10 | 0 |
|  | 0.1 | 10 | 10 | 10 | 10 | 0 |
|  | 0.2 | 10 | 10 | 10 | 10 | 0 |
|  | 0.4 | 10 | 10 | 10 | 10 | 0 |
| 6 | 0.025 | 8 | 8 | 8 | 9 | 0 |
|  | 0.05 | 10 | 9 | 9 | 10 | 0 |
|  | 0.1 | 10 | 10 | 10 | 10 | 0 |
|  | 0.2 | 10 | 10 | 10 | 10 | 0 |

TABLE 2-continued

| Compound No. | Application rate, kg/ha | Echinochloa crusgalli | Monochoria (Monochoria vaginalis) | False Bulrush (Scirpus juncoides) | pimpernel (Lindernia pyxidaria) | Rice (Oryza sativa) |
|---|---|---|---|---|---|---|
|  | 0.4 | 10 | 10 | 10 | 10 | 1 |
| 7 | 0.025 | 9 | 8 | 9 | 9 | 0 |
|  | 0.05 | 10 | 9 | 10 | 10 | 0 |
|  | 0.1 | 10 | 10 | 10 | 10 | 0 |
|  | 0.2 | 10 | 10 | 10 | 10 | 0 |
|  | 0.4 | 10 | 10 | 10 | 10 | 1 |
| 8 | 0.025 | 8 | 8 | 8 | 9 | 0 |
|  | 0.05 | 9 | 10 | 9 | 10 | 0 |
|  | 0.1 | 10 | 10 | 10 | 10 | 0 |
|  | 0.2 | 10 | 10 | 10 | 10 | 0 |
|  | 0.4 | 10 | 10 | 10 | 10 | 1 |
| 9 | 0.025 | 10 | 8 | 8 | 9 | 0 |
|  | 0.05 | 10 | 9 | 9 | 10 | 0 |
|  | 0.1 | 10 | 10 | 10 | 10 | 0 |
|  | 0.2 | 10 | 10 | 10 | 10 | 0 |
|  | 0.4 | 10 | 10 | 10 | 10 | 0 |
| 10 | 0.025 | 9 | 8 | 9 | 8 | 0 |
|  | 0.05 | 10 | 9 | 10 | 10 | 0 |
|  | 0.1 | 10 | 10 | 10 | 10 | 0 |
|  | 0.2 | 10 | 10 | 10 | 10 | 0 |
|  | 0.4 | 10 | 10 | 10 | 10 | 1 |
| 11 | 0.025 | 10 | 8 | 9 | 8 | 0 |
|  | 0.05 | 10 | 9 | 10 | 9 | 0 |
|  | 0.1 | 10 | 10 | 10 | 10 | 0 |
|  | 0.2 | 10 | 10 | 10 | 10 | 0 |
|  | 0.4 | 10 | 10 | 10 | 10 | 0 |
| 12 | 0.025 | 10 | 8 | 8 | 8 | 0 |
|  | 0.05 | 10 | 9 | 10 | 9 | 0 |
|  | 0.1 | 10 | 10 | 10 | 10 | 0 |
|  | 0.2 | 10 | 10 | 10 | 10 | 0 |
|  | 0.4 | 10 | 10 | 10 | 10 | 1 |
| 13 | 0.025 | 8 | 8 | 8 | 8 | 0 |
|  | 0.05 | 9 | 9 | 9 | 10 | 0 |
|  | 0.1 | 10 | 10 | 10 | 10 | 0 |
|  | 0.2 | 10 | 10 | 10 | 10 | 0 |
|  | 0.4 | 10 | 10 | 10 | 10 | 1 |
| 14 | 0.025 | 8 | 8 | 8 | 9 | 0 |
|  | 0.05 | 9 | 9 | 9 | 10 | 0 |
|  | 0.1 | 10 | 10 | 10 | 10 | 0 |
|  | 0.2 | 10 | 10 | 10 | 10 | 1 |
|  | 0.4 | 10 | 10 | 10 | 10 | 2 |
| 15 | 0.025 | 8 | 8 | 8 | a | 0 |
|  | 0.05 | 10 | 9 | 9 | 9 | 0 |
|  | 0.1 | 10 | 10 | 10 | 10 | 0 |
|  | 0.2 | 10 | 10 | 10 | 10 | 0 |
|  | 0.4 | 10 | 10 | 10 | 10 | 2 |
| A | 0.025 | 7 | 7 | 7 | 7 | 1 |
|  | 0.05 | 8 | 8 | 9 | 8 | 2 |
|  | 0.1 | 9 | 9 | 10 | 9 | 4 |
|  | 0.2 | 10 | 10 | 10 | 10 | 5 |
|  | 0.4 | 10 | 10 | 10 | 10 | 6 |
| B | 0.025 | 6 | 7 | 8 | 6 | 1 |
|  | 0.05 | 8 | 8 | 9 | 8 | 2 |
|  | 0.1 | 9 | 9 | 10 | 9 | 3 |
|  | 0.2 | 10 | 10 | 10 | 10 | 5 |
|  | 0.4 | 10 | 10 | 10 | 10 | 6 |

PHYSIOLOGICAL TEST 3

Pharmaceutically Injurious Action Test by Change of Planting Depth of Paddy Rice 1/500000-hectare Wagner pots were filled with soil, and they were put in water and the soil was then tilled. Afterward, two pairs of paddy rice (Oryza sativa) seedlings (2-3 leaf stage), which had been reared in advance, were transplanted to each pot at planting depths of 1 cm and 2 cm and were allowed to grow in a green house, each pair being constituted of two rice seedlings. One day later, each pot was treated with a wettable powder which had been prepared by processing a predetermined amount of the test compound in accordance with the procedure described in Formulation Example 2. A submerged portion of each rice seedling was kept at 3 cm, and afterward, the paddy rice seedlings were also allowed to grow in the green house. The growing state of weeds and the injurious state to the rice were observed 30 days later. The results are summarized in Table 3. In this table, the injurious degree to the paddy rice is denoted in the same manner as in Physiological Test 1.

Table 3 indicates that in this test, the herbicidal compositions regarding the present invention exerted excellent safety even to the paddy rice planted at a depth of 1 cm. On the contrary, Comparative Compounds A and B had a pharmaceutically injurious strong action on the paddy rice at a depth of 1 cm even in treatments at low application rates.

TABLE 3

| Compound No. | Application Rate (kg/ha) | Paddy Rice (planting at depth of 2 cm) | Paddy Rice (planting at depth of 1 cm) |
|---|---|---|---|
| 1 | 0.025 | 0 | 0 |
|   | 0.05  | 0 | 0 |
|   | 0.1   | 0 | 0 |
|   | 0.2   | 0 | 0 |
| 2 | 0.025 | 0 | 0 |
|   | 0.05  | 0 | 0 |
|   | 0.1   | 0 | 0 |
|   | 0.2   | 0 | 1 |
| 3 | 0.025 | 0 | 0 |
|   | 0.05  | 0 | 0 |
|   | 0.1   | 0 | 0 |
|   | 0.2   | 0 | 0 |
| 4 | 0.025 | 0 | 0 |
|   | 0.05  | 0 | 0 |
|   | 0.1   | 0 | 0 |
|   | 0.2   | 0 | 0 |
| 5 | 0.025 | 0 | 0 |
|   | 0.05  | 0 | 0 |
|   | 0.1   | 0 | 0 |
|   | 0.2   | 0 | 1 |
| 6 | 0.025 | 0 | 0 |
|   | 0.05  | 0 | 0 |
|   | 0.1   | 0 | 0 |
|   | 0.2   | 0 | 1 |
| 7 | 0.025 | 0 | 0 |
|   | 0.05  | 0 | 0 |
|   | 0.1   | 0 | 1 |
|   | 0.2   | 0 | 2 |
| 8 | 0.025 | 0 | 0 |
|   | 0.05  | 0 | 0 |
|   | 0.1   | 0 | 0 |
|   | 0.2   | 0 | 2 |
| 9 | 0.025 | 0 | 0 |
|   | 0.05  | 0 | 0 |
|   | 0.1   | 0 | 0 |
|   | 0.2   | 0 | 0 |
| 10 | 0.025 | 0 | 0 |
|    | 0.05  | 0 | 0 |
|    | 0.1   | 0 | 0 |
|    | 0.2   | 0 | 0 |
| 11 | 0.025 | 0 | 0 |
|    | 0.05  | 0 | 0 |
|    | 0.1   | 0 | 0 |
|    | 0.2   | 0 | 0 |
| 12 | 0.025 | 0 | 0 |
|    | 0.05  | 0 | 0 |
|    | 0.1   | 0 | 0 |
|    | 0.2   | 0 | 1 |
| 13 | 0.025 | 0 | 0 |
|    | 0.05  | 0 | 0 |
|    | 0.1   | 0 | 1 |
|    | 0.2   | 0 | 2 |
| 14 | 0.025 | 0 | 0 |
|    | 0.05  | 0 | 0 |
|    | 0.1   | 0 | 1 |
|    | 0.2   | 0 | 2 |
| 15 | 0.025 | 0 | 0 |
|    | 0.05  | 0 | 0 |
|    | 0.1   | 0 | 0 |
|    | 0.2   | 0 | 2 |
| A  | 0.025 | 0 | 2 |
|    | 0.05  | 0 | 3 |
|    | 0.1   | 2 | 4 |
|    | 0.2   | 3 | 8 |
| B  | 0.025 | 0 | 1 |
|    | 0.05  | 1 | 3 |
|    | 0.1   | 3 | 4 |
|    | 0.2   | 4 | 7 |

PHYSIOLOGICAL TEST 4

Treatment of Soil Under Submerged Condition (Pre-emergence Treatment)

1/500000-hectare Wagner pots were filled with soil, and they were put in water and the soil was then tilled. Afterward, seeds of *Echinochloa crusgalli*, bulrush (*Scirpus juncoides*), monochoria (*Monochoria vaginalis*) and false pimpernel (*Lindernia pyxidaria*) were sown under submerged condition. Two pairs of paddy rice (*Oryza sativa*) seedlings (2-3 leaf stage), which had been reared in advance, were transplanted to each pot and were allowed to grow in a green house, each pair being constituted of two rice seedlings. One day later (before the emergence of weeds), each pot was treated with a wettable powder which had been prepared by processing a predetermined amount of the test compound in accordance with the procedure described in Formulation Example 9. A submerged portion of each rice seedling was set to 3 cm, and from the next day after the treatment, water leak was carried out for 10 days. That is, water in each pot was allowed to drop through the bottom of the pot by the use of a glass tube so that a water surface might go down as much as 1 cm per day. The growing state of weeds and the injurious state to the rice were observed 30 days later. The results are summarized in Table 4. In this table, the damage degree of each test plant and the injurious degree to the paddy rice are denoted in accordance with standards shown in Physiological Test 1.

TABLE 4

| Compound No. | Application rate, kg/ha | *Echinochloa crusgalli* | Monochoria (*Monochoria vaginalis*) | False Bulrush (*Scirpus juncoides*) | pimpernel (*Lindernia pyxidaria*) | Rice (*Oryza sativa*) |
|---|---|---|---|---|---|---|
| 16 | 0.025 | 10 | 9  | 10 | 9  | 0 |
|    | 0.05  | 10 | 10 | 10 | 10 | 0 |
|    | 0.1   | 10 | 10 | 10 | 10 | 0 |
|    | 0.2   | 10 | 10 | 10 | 10 | 1 |
| 17 | 0.025 | 10 | 10 | 10 | 10 | 0 |
|    | 0.05  | 10 | 10 | 10 | 10 | 0 |
|    | 0.1   | 10 | 10 | 10 | 10 | 0 |
|    | 0.2   | 10 | 10 | 10 | 10 | 1 |
| 18 | 0.025 | 10 | 10 | 10 | 10 | 0 |
|    | 0.05  | 10 | 10 | 10 | 10 | 0 |
|    | 0.1   | 10 | 10 | 10 | 10 | 0 |
|    | 0.2   | 10 | 10 | 10 | 10 | 0 |
| 19 | 0.025 | 10 | 10 | 10 | 10 | 0 |
|    | 0.05  | 10 | 10 | 10 | 10 | 0 |
|    | 0.1   | 10 | 10 | 10 | 10 | 0 |
|    | 0.2   | 10 | 10 | 10 | 10 | 1 |
| A  | 0.025 | 8  | 7  | 8  | 7  | 1 |

TABLE 4-continued

| Compound No. | Application rate, kg/ha | Echinochloa crusgalli | Monochoria (Monochoria vaginalis) | False Bulrush (Scirpus juncoides) | pimpernel (Lindernia pyxidaria) | Rice (Oryza sativa) |
| --- | --- | --- | --- | --- | --- | --- |
|  | 0.05 | 9 | 8 | 9 | 8 | 2 |
|  | 0.1 | 10 | 10 | 10 | 9 | 4 |
|  | 0.2 | 10 | 10 | 10 | 10 | 6 |
| C | 0.025 | 8 | 7 | 9 | 8 | 1 |
|  | 0.05 | 10 | 9 | 10 | 9 | 3 |
|  | 0.1 | 10 | 10 | 10 | 10 | 5 |
|  | 0.2 | 10 | 10 | 10 | 10 | 6 |

Table 4 indicates that in this test, the herbicidal compositions regarding the present invention exerted higher herbicidal effects to the sample weeds in the paddy fields in spite of the low application rates, and they also exerted excellent safety to the paddy rice. On the contrary, Comparative Compounds A and B had a pharmaceutically injurious action on the paddy rice, when they were used in amounts capable of completely killing the weeds.

PHYSIOLOGICAL TEST 5

Treatment of Soil Under Submerged Condition
(Growing Period Treatment)

1/500000-hectare Wagner pots were filled with soil, and they were put in water and the soil was then tilled. Afterward, seeds of Echinochloa crusgalli, bulrush (Scirpus juncoides), monochoria (Monochoria vaginalis) and false pimpernel (Lindernia pyxidaria) were sown under submerged condition. Two pairs of paddy rice (Oryza sativa) seedlings (2–3 leaf stage), which had been reared in advance, were transplanted to each pot and were allowed to grow in a green house, each pair being constituted of two rice seedlings. When Echinochloa crusgalli became bifoliate, each pot was treated with a wettable powder which had been prepared by processing a predetermined amount of the test compound in accordance with the procedure described in Formulation Example 10. A submerged portion of each rice seedling was set to 3 cm, and from the next day after the treatment, water leak was carried out for 10 days. That is, water in each pot was allowed to drop through the bottom of the pot by the use of a glass tube so that a water surface might go down as much as 1 cm per day. The growing state of weeds and the injurious state to the rice were observed 30 days later. The results are summarized in Table 5. In this table, the damage degree of each test plant and the injurious degree to the paddy rice are denoted in the same manner as in Physiological Test 1.

TABLE 5

| Compound No. | Application rate, kg/ha | Echinochloa crusgalli | Monochoria (Monochoria vaginalis) | False Bulrush (Scirpus juncoides) | pimpernel (Lindernia pyxidaria) | Rice (Oryza sativa) |
| --- | --- | --- | --- | --- | --- | --- |
| 16 | 0.025 | 8 | 7 | 9 | 7 | 0 |
|  | 0.05 | 10 | 9 | 10 | 9 | 0 |
|  | 0.1 | 10 | 10 | 10 | 10 | 0 |
|  | 0.2 | 10 | 10 | 10 | 10 | 0 |
|  | 0.4 | 10 | 10 | 10 | 10 | 1 |
| 17 | 0.025 | 9 | 8 | 9 | 9 | 0 |
|  | 0.05 | 10 | 9 | 10 | 10 | 0 |
|  | 0.1 | 10 | 10 | 10 | 10 | 0 |
|  | 0.2 | 10 | 10 | 10 | 10 | 0 |
|  | 0.4 | 10 | 10 | 10 | 10 | 1 |
| 18 | 0.025 | 9 | 9 | 9 | 8 | 0 |
|  | 0.05 | 10 | 10 | 10 | 9 | 0 |
|  | 0.1 | 10 | 10 | 10 | 10 | 0 |
|  | 0.2 | 10 | 10 | 10 | 10 | 0 |
|  | 0.4 | 10 | 10 | 10 | 10 | 1 |
| 19 | 0.025 | 9 | 9 | 9 | 8 | 0 |
|  | 0.05 | 10 | 10 | 10 | 9 | 0 |
|  | 0.1 | 10 | 10 | 10 | 10 | 0 |
|  | 0.2 | 10 | 10 | 10 | 10 | 0 |
|  | 0.4 | 10 | 10 | 10 | 10 | 1 |
| A | 0.025 | 7 | 7 | 7 | 7 | 1 |
|  | 0.05 | 8 | 8 | 9 | 8 | 2 |
|  | 0.1 | 9 | 9 | 10 | 9 | 4 |
|  | 0.2 | 10 | 10 | 10 | 10 | 5 |
|  | 0.4 | 10 | 10 | 10 | 10 | 6 |
| C | 0.025 | 7 | 7 | 8 | 7 | 1 |
|  | 0.05 | 9 | 8 | 9 | 8 | 2 |
|  | 0.1 | 10 | 9 | 10 | 10 | 3 |
|  | 0.2 | 10 | 10 | 10 | 10 | 5 |
|  | 0.4 | 10 | 10 | 10 | 10 | 6 |

Table 5 indicates that in this test, the herbicidal compositions regarding the present invention exerted higher herbicidal effects to the sample weeds in the paddy fields in spite of the low application rates, and they also exerted excellent safety to the paddy rice. On the contrary, Comparative Compounds A and B had a pharmaceutically injurious action on the paddy rice, when they were used in amounts capable of completely killing the weeds.

PHYSIOLOGICAL TEST 6

Pharmaceutically Injurious Action Test by Change of Planting Depth of Paddy Rice 1/500000-hectare Wagner pots were filled with soil, and they were put in water and the soil was then tilled. Afterward, two pairs of paddy rice (*Oryza sativa*) seedlings (2–3 leaf stage), which had been reared in advance, were transplanted to each pot at planting depths of 1 cm and 2 cm and were allowed to grow in a green house, each pair being constituted of two rice seedlings. One day later, each pot was treated with a wettable powder which had been prepared by processing a predetermined amount of the test compound in accordance with the procedure described in Formulation Example 10. A submerged portion of each rice seedling was kept at 3 cm, and afterward, the paddy rice seedlings were also allowed to grow in the green house. The growing state of weeds and the injurious state to the rice were observed 30 days later. The results are summarized in Table 6. In this table, the injurious degree to the paddy rice is denoted in the same manner as in Physiological Test 1.

TABLE 6

| Compound No. | Application Rate (kg/ha) | Paddy Rice (planting at depth of 2 cm) | Paddy Rice (planting at depth of 1 cm) |
|---|---|---|---|
| 16 | 0.025 | 0 | 0 |
|    | 0.05  | 0 | 0 |
|    | 0.1   | 0 | 0 |
|    | 0.2   | 0 | 1 |
| 17 | 0.025 | 0 | 0 |
|    | 0.05  | 0 | 0 |
|    | 0.1   | 0 | 0 |
|    | 0.2   | 0 | 1 |
| 18 | 0.025 | 0 | 0 |
|    | 0.05  | 0 | 0 |
|    | 0.1   | 0 | 0 |
|    | 0.2   | 0 | 0 |
| 19 | 0.025 | 0 | 0 |
|    | 0.05  | 0 | 0 |
|    | 0.1   | 0 | 0 |
|    | 0.2   | 0 | 1 |
| A  | 0.025 | 0 | 2 |
|    | 0.05  | 0 | 3 |
|    | 0.1   | 2 | 4 |
|    | 0.2   | 3 | 8 |
| C  | 0.025 | 0 | 1 |
|    | 0.05  | 1 | 3 |
|    | 0.1   | 3 | 4 |
|    | 0.2   | 4 | 7 |

Table 6 indicates that in this test, the herbicidal compositions regarding the present invention exerted excellent safety even to the paddy rice planted at a depth of 1 cm. On the contrary, Comparative Compounds A and B had a pharmaceutically injurious strong action on the paddy rice at a depth of 1 cm even in treatments at low application rates.

PHYSIOLOGICAL TEST 7

Treatment of Soil Under Submerged Condition (Pre-emergence Treatment)

1/500000-hectare Wagner pots were filled with soil, and they were put in water and the soil was then tilled. Afterward, seeds of *Echinochloa crusgalli*, bulrush (*Scirpus juncoides*), monochoria (*Monochoria vaginalis*) and false pimpernel (*Lindernia pyxidaria*) were sown under submerged condition. Two pairs of paddy rice (*Oryza sativa*) seedlings (2–3 leaf stage), which had been reared in advance, were transplanted to each pot and were allowed to grow in a green house, each pair being constituted of two rice seedlings. One day later (before the emergence of weeds), each pot was treated with a wettable powder which had been prepared by processing a predetermined amount of the test compound in accordance with the procedure described in Formulation Example 17. A submerged portion of each rice seedling was set to 3 cm, and from the next day after the treatment, water leak was carried out for 10 days. That is, water in each pot was allowed to drop through the bottom of the pot by the use of a glass tube so that a water surface might go down as much as 1 cm per day. The growing state of weeds and the injurious state to the rice were observed 30 days later. The results are summarized in Table 7. In this table, the damage degree of each test plant and the injurious degree to the paddy rice are denoted in accordance with standards shown in Physiological Test 1.

TABLE 7

| Compound No. | Application rate, kg/ha | *Echinochloa crusgalli* | Monochoria (*Monochoria vaginalis*) | False Bulrush (*Scirpus juncoides*) | pimpernel (*Lindernia pyxidaria*) | Rice (*Oryza sativa*) |
|---|---|---|---|---|---|---|
| 21 | 0.025 | 10 | 9  | 9  | 9  | 0 |
|    | 0.05  | 10 | 10 | 10 | 10 | 0 |
|    | 0.1   | 10 | 10 | 10 | 10 | 0 |
|    | 0.2   | 10 | 10 | 10 | 10 | 0 |
| 22 | 0.025 | 8  | 9  | 9  | 8  | 0 |
|    | 0.05  | 9  | 10 | 10 | 9  | 0 |
|    | 0.1   | 10 | 10 | 10 | 10 | 0 |
|    | 0.2   | 10 | 10 | 10 | 10 | 0 |
| A  | 0.025 | 8  | 7  | 8  | 7  | 1 |
|    | 0.05  | 9  | 8  | 9  | 8  | 2 |
|    | 0.1   | 10 | 10 | 10 | 9  | 4 |
|    | 0.2   | 10 | 10 | 10 | 10 | 6 |
| B  | 0.025 | 7  | 7  | 7  | 8  | 1 |
|    | 0.05  | 8  | 8  | 9  | 9  | 3 |
|    | 0.1   | 9  | 9  | 10 | 10 | 4 |
|    | 0.2   | 10 | 10 | 10 | 10 | 6 |

Table 7 indicates that in this test, the herbicidal compositions regarding the present invention exerted higher herbicidal effects to the sample weeds in the paddy fields in spite of the low application rates, and they also exerted excellent safety to the paddy rice. On the contrary, Comparative Compounds A and B had a pharmaceutically injurious action on the paddy rice, when they were used in amounts capable of completely killing the weeds.

PHYSIOLOGICAL TEST 8

Treatment of Soil Under Submerged Condition
(Growing Period Treatment)

1/500000-hectare Wagner pots were filled with soil, and they were put in water and the soil was then tilled. Afterward, seeds of Echinochloa crusgalli, bulrush (Scirpus juncoides), monochoria (Monochoria vaginalis) and false pimpernel (Lindernia pyxidaria) were sown under submerged condition. Two pairs of paddy rice (Oryza sativa) seedlings (2–3 leaf stage), which had been reared in advance, were transplanted to each pot and were allowed to grow in a green house, each pair being constituted of two rice seedlings. When Echinochloa crusgalli became bifoliate, each pot was treated with a wettable powder which had been prepared by processing a predetermined amount of the test compound in accordance with the procedure described in Formulation Example 18. A submerged portion of each rice seedling was set to 3 cm, and from the next day after the treatment, water leak was carried out for 10 days. That is, water in each pot was allowed to drop through the bottom of the pot by the use of a glass tube so that a water surface might go down as much as 1 cm per day. The growing state of weeds and the injurious state to the rice were observed 30 days later. The results are summarized in Table 8. In this table, the damage degree of each test plant and the injurious degree to the paddy rice are denoted in the same manner as in Physiological Test 1.

PHYSIOLOGICAL TEST 9

Pharmaceutically Injurious Action Test by Change of Planting Depth of Paddy Rice 1/500000-hectare Wagner pots were filled with soil, and they were put in water and the soil was then tilled. Afterward, two pairs of paddy rice (Oryza sativa) seedlings (2–3 leaf stage), which had been reared in advance, were transplanted to each pot at planting depths of 1 cm and 2 cm and were allowed to grow in a green house, each pair being constituted of two rice seedlings. One day later, each pot was treated with a wettable powder which had been prepared by processing a predetermined amount of the test compound in accordance with the procedure described in Formulation Example 18. A submerged portion of each rice seedling was kept at 3 cm, and afterward, the paddy rice seedlings were also allowed to grow in the green house. The growing state of weeds and the injurious state to the rice were observed 30 days later. The results are summarized in Table 9. In this table, the injurious degree to the paddy rice is denoted in the same manner as in Physiological Test 1.

TABLE 9

| Compound No. | Application Rate (kg/ha) | Paddy Rice (planting at depth of 2 cm) | Paddy Rice (planting at depth of 1 cm) |
|---|---|---|---|
| 21 | 0.025 | 0 | 0 |
|  | 0.05 | 0 | 0 |
|  | 0.1 | 0 | 0 |
|  | 0.2 | 0 | 0 |
| 22 | 0.025 | 0 | 0 |
|  | 0.05 | 0 | 0 |
|  | 0.1 | 0 | 0 |
|  | 0.2 | 0 | 1 |
| A | 0.025 | 0 | 2 |
|  | 0.05 | 0 | 3 |
|  | 0.1 | 2 | 4 |
|  | 0.2 | 3 | 8 |
| B | 0.025 | 0 | 1 |
|  | 0.05 | 1 | 3 |
|  | 0.1 | 3 | 4 |
|  | 0.2 | 4 | 7 |

TABLE 8

| Compound No. | Application rate, kg/ha | Echinochloa crusgalli | Monochoria (Monochoria vaginalis) | False Bulrush (Scirpus juncoides) | pimpernel (Lindernia pyxidaria) | Rice (Oryza sativa) |
|---|---|---|---|---|---|---|
| 21 | 0.025 | 9 | 8 | 9 | 8 | 0 |
|  | 0.05 | 10 | 9 | 10 | 9 | 0 |
|  | 0.1 | 10 | 10 | 10 | 10 | 0 |
|  | 0.2 | 10 | 10 | 10 | 10 | 0 |
|  | 0.4 | 10 | 10 | 10 | 10 | 0 |
| 22 | 0.025 | 8 | 8 | 8 | 7 | 0 |
|  | 0.05 | 9 | 9 | 9 | 8 | 0 |
|  | 0.1 | 10 | 10 | 10 | 10 | 0 |
|  | 0.2 | 10 | 10 | 10 | 10 | 0 |
|  | 0.4 | 10 | 10 | 10 | 10 | 0 |
| A | 0.025 | 7 | 7 | 7 | 7 | 1 |
|  | 0.05 | 8 | 8 | 9 | 8 | 2 |
|  | 0.1 | 9 | 9 | 10 | 9 | 4 |
|  | 0.2 | 10 | 10 | 10 | 10 | 5 |
|  | 0.4 | 10 | 10 | 10 | 10 | 6 |
| B | 0.025 | 6 | 7 | 8 | 6 | 1 |
|  | 0.05 | 8 | 8 | 9 | 8 | 2 |
|  | 0.1 | 9 | 9 | 10 | 9 | 3 |
|  | 0.2 | 10 | 10 | 10 | 10 | 5 |
|  | 0.4 | 10 | 10 | 10 | 10 | 6 |

Table 8 indicates that in this test, the herbicidal compositions regarding the present invention exerted higher herbicidal effects to the sample weeds in the paddy fields in spite of the low application rates, and they also exerted excellent safety to the paddy rice. On the contrary, Comparative Compounds A and B had a pharmaceutically injurious action on the paddy rice, when they were used in amounts capable of completely killing the weeds.

Table 9 indicates that in this test, the herbicidal compositions regarding the present invention exerted excellent safety even to the paddy rice planted at a depth of 1 cm. On the contrary, Comparative Compounds A and B had a pharmaceutically injurious strong action on the paddy rice at a depth of 1 cm even in treatments at low application rates.

As described above in detail, a 3-pyrroline-2-one derivative represented by the formula (I) regarding the present invention is a novel compound, and a herbicidal composition containing this compound has a herbicidal activity on various kinds of troublesome weeds in paddy fields in a low application rate in a wide period of from the pre-emergence of the weeds to the growing period of the emerged weeds. Furthermore, this compound shows an excellent selectivity to rice, and so it is always stably selective even in the paddy fields of water leak and to the shallowly planted paddy rice, so that the above-mentioned compound can be safely used.

What is claimed is:

1. A 1-[1-methyl-1-(substituted phenyl)ethyl]-4,5-dimethyl-3-(substituted phenyl)-3-pyrroline-2-one derivative represented by the formula (I)

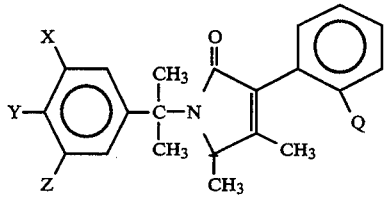

(I)

wherein X is a chlorine atom, fluorine atom or bromine atom; Y is a hydrogen atom, fluorine atom, chlorine atom or methoxy group; Z is a hydrogen atom, fluorine atom, bromine atom or chlorine atom; and Q is a hydrogen atom or fluorine atom.

2. The 1-[1-methyl-1-(substituted phenyl)ethyl]-4,5-dimethyl-3-(substituted phenyl)-3-pyrroline-2-one derivative according to claim 1 wherein in the formula (I)

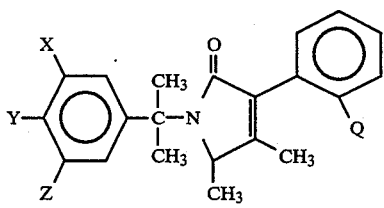

(I)

X is a chlorine atom; Y is a hydrogen atom; Z is a hydrogen atom or chlorine atom; and Q is a hydrogen atom or fluorine atom.

3. The 1-[1-methyl-1-(substituted phenyl)ethyl]-4,5-dimethyl-3-(substituted phenyl)-3-pyrroline-2-one derivative according to claim 1 wherein in the formula (I)

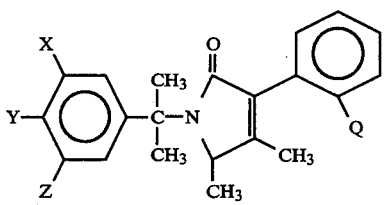

(I)

each of X and Y is a chlorine atom; Z is a hydrogen atom; and Q is a hydrogen atom or fluorine atom.

4. A herbicidal composition comprising a 1-[1-methyl-1-(substituted phenyl)ethyl]-4,5-dimethyl-3(substituted phenyl)-3-pyrroline-2-one derivative represented by the formula (I)

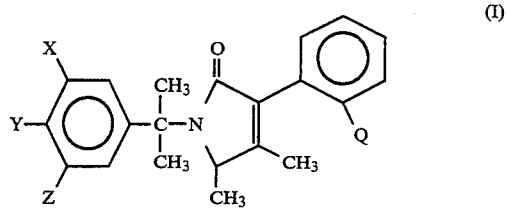

(I)

wherein X is a chlorine atom, fluorine atom or bromine atom; Y is a hydrogen atom, fluorine atom, chlorine atom or methoxy group; Z is a hydrogen atom, fluorine atom, bromine atom or chlorine atom; and Q is a hydrogen atom or fluorine atom, and a diluent or a carrier for the herbicidal composition.

5. The herbicidal composition according to claim 4 wherein said herbicidal composition is a wettable powder containing 1 to 50% by weight of 1-[1-methyl-1-(substituted phenyl)ethyl]-4,5-dimethyl-3-(substituted phenyl)-3-pyrroline-2-one derivative represented by the formula (I).

6. The herbicidal composition according to claim 4 wherein said herbicidal composition is a powder containing 0.01 to 20% by weight of 1-[1-methyl-1-(substituted phenyl)ethyl]-4,5-dimethyl-3-(substituted phenyl)-3-pyrroline-2-one derivative represented by the formula (I).

7. The herbicidal composition according to claim 4 wherein said herbicidal composition is granules containing 0.01 to 10% by weight of 1-[1-methyl-1-(substituted phenyl)ethyl]-4,5-dimethyl-3-(substituted phenyl)-3-pyrroline-2-one derivative represented by the formula (I).

8. The herbicidal composition according to claim 4 wherein said herbicidal composition is an emulsion containing 0.1 to 50% by weight of 1-[1-methyl-1-(substituted phenyl)ethyl]-4,5-dimethyl-3-(substituted phenyl)-3-pyrroline-2-one derivative represented by the formula (I).

9. The herbicidal composition according to claim 4 wherein said herbicidal composition is a flowable formulation containing 0.1 to 50% by weight of 1-[1-methyl-1-(substituted phenyl)ethyl]-4,5-dimethyl-3-(substituted phenyl)-3-pyrroline-2-one derivative represented by the formula (I).

10. A use for spraying a 1-[1-methyl-1-(substituted phenyl)ethyl]-4,5-dimethyl-3-(substituted phenyl)-3-pyrroline-2-one derivative represented by the formula (I)

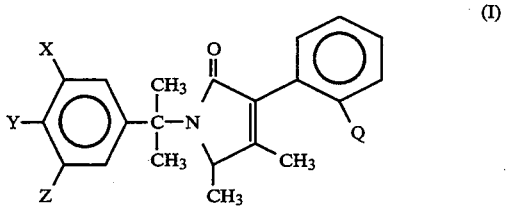

(I)

wherein X is a chlorine atom, fluorine atom or bromine atom; Y is a hydrogen atom, fluorine atom, chlorine atom or methoxy group; Z is a hydrogen atom, fluorine atom, bromine atom or chlorine atom; and Q is a hydrogen atom or fluorine atom, on a paddy field in an amount of from 0.005 to 2 kg/ha.

* * * * *